United States Patent [19]

Karydas

[11] Patent Number: 4,836,958

[45] Date of Patent: Jun. 6, 1989

[54] FLUORINATED CATIONIC COMPOUNDS

[75] Inventor: Athanasios Karydas, Brooklyn, N.Y.

[73] Assignee: Ciba-Geigy Corporation, Ardsley, N.Y.

[21] Appl. No.: 892,216

[22] Filed: Jul. 31, 1986

[51] Int. Cl.[4] .................. C07C 147/02; C07C 147/14; C07C 149/24

[52] U.S. Cl. .............................. 260/501.15; 544/58.1; 544/59; 544/158; 544/159; 544/160; 544/161; 544/398; 544/399; 544/400; 546/246; 546/247; 546/248; 548/567; 548/569; 558/413; 558/414; 558/422; 558/437; 558/438; 560/227; 564/96; 564/97; 564/209; 564/212; 564/292; 564/293; 564/373; 564/375; 564/500; 564/501

[58] Field of Search ................. 564/285, 292, 293, 96, 564/97, 209, 212; 558/413, 414, 422, 437, 438; 560/227; 260/501.15

[56] References Cited

U.S. PATENT DOCUMENTS

| | | | |
|---|---|---|---|
| 2,727,923 | 12/1955 | Husted | 260/567.6 |
| 3,350,218 | 10/1967 | Gagliardi | 117/76 |
| 3,883,596 | 5/1975 | Hager | 260/609 R |
| 4,577,036 | 3/1986 | Falk | 549/556 |
| 4,638,089 | 1/1987 | Hisamoto et al. | 564/292 |

*Primary Examiner*—Richard L. Raymond
*Attorney, Agent, or Firm*—JoAnn Villamizar; Irving M. Fishman

[57] ABSTRACT

The instant invention relates to fluorinated cationic compounds of the formula

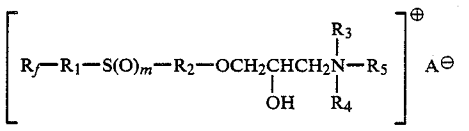

(I)

wherein $R_f$ is a perfluoroalkyl or perfluoroalkoxy-perfluoroalkyl group;

$R_1$ is alkylene optionally interrupted by —O—, —S—, $—SO_2—$, $—SO_2NR'—$, $—CO_2—$, —NR'—, or —CONR'— where R' is hydrogen or lower alkyl;

m is 0, 1 or 2;

$R_2$ is linear or branched alkylene;

$R_3$, $R_4$, and $R_5$ independently of one another represent alkyl or arylalkyl groups which are unsubstituted or substituted by hydroxyl, lower alkoxy, halogen, cyano or by polyalkyleneoxy, or $R_3$ and $R_4$ together with the nitrogen atom to which they are attached represent a 5- or 6-membered heterocyclic radical or $R_3$, $R_4$ and $R_5$ together with nitrogen atom that links them represent a substituted or unsubstituted pyridine ring; and $A^{\ominus}$ represents the anion of an organic or inorganic acid; and their particular use as surfactants.

16 Claims, No Drawings

FLUORINATED CATIONIC COMPOUNDS

BACKGROUND OF THE INVENTION

The present invention relates to novel fluorinated cationic compounds and their use as surfactants in aqueous media, including fresh and sea water.

A number of diverse fluorinated cationic compounds are known in the art. For example, U.S. Pat. No. 2,727,923 discloses quaternary ammonium compounds of the general formula

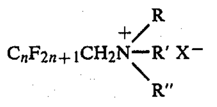

where n is an integer in the range of three to nine; R, R' and R" are alkyl of one to five carbon atoms and X is an anion. Such compounds are clearly diverse from those of the instant invention.

Also, U.S. Pat. No. 3,350,218 discloses certain quaternary ammonium derivatives of fluoroaliphatic carboxamidoalkyleneamines.

In addition, U.S. Pat. No. 3,883,596 discloses secondary and tertiary amines prepared by reacting a primary or secondary alkyl amine with a fluoroalkylthiopropylene oxide and states that amines can be converted to ammonium salts. However, there is no disclosure therein of any quaternary ammonium compounds of the type described by the instant invention, nor is there any suggestion of any compounds containing the instant perfluoroalkyl-alkyl-thio-(sulfinyl- or sulfonyl-)alkyleneoxy quaternary ammonium derivatives.

Also, U.S. Pat. No. 4,577,036 relates to perfluoroalkyl-alkylthio(sulfinyl or sulfonyl)alkylene glycidyl ethers as well as the use thereof in preparing the corresponding sulfato betaine and amino acid derivatives. However, there is no disclosure of the instant class of quaternary derivatives.

DETAILED DESCRIPTION OF THE INVENTION

The instant invention relates to fluorinated cationic compounds of the formula

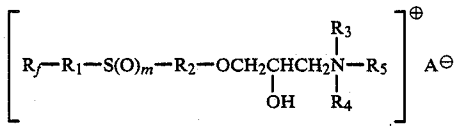

(I)

wherein $R_f$ is a perfluoroalkyl or perfluoroalkyl-perfluoroalkyl group;

$R_1$ is alkylene optionally interrupted by —O—, —S—, $SO_2$, $SO_2NR'$, —$CO_2$—, —NR'—, or —CONR'— where R' is hydrogen or lower alkyl;

m is 0, 1 or 2;

$R_2$ is linear or branched alkylene;

$R_3$, $R_4$, and $R_5$ independently of one another represent alkyl or aralkyl groups which are unsubstituted or substituted by hydroxyl, halogen, cyano, lower alkoxy or by poly-lower alkyleneoxy, or $R_3$ and $R_4$ together with the nitrogen atom to which they are attached represent a 5- or 6-membered heterocyclic radical or $R_3$, $R_4$, and $R_5$ together with nitrogen atom that links them represent a substituted or unsubstituted pyridine ring; and $A^{\ominus}$ represents the anion of an organic or inorganic acid;

and their usefulness as surfactants.

In formula (I), $R_f$ represents preferably a perfluoroalkyl group of 3 to 18, preferably 6 to 10 carbon atoms. Examples of perfluoroalkyl group $R_f$ are perfluoropropyl, perfluorobutyl, perfluoropentyl, perfluorohexyl, perfluorooctyl, perfluorodecyl, perfluorododecyl, perfluorotetradecyl, perfluorohexadecyl or perfluorooctadecyl. When substituted by perfluoroalkoxy, the perfluoroalkoxy group may have 1–18 carbon atoms.

In a preferred embodiment the radical $R_1$ is alkylene of 1 to 7 carbon atoms and most preferably ethylene.

Preferably, m is 0 or 2.

The radical $R_2$ is a lower alkylene, preferably $C_2$–$C_4$ alkylene, more preferably propylene or isopropylene.

The radicals $R_3$, $R_4$, and $R_5$ can be different from each other but preferably they are identical. When radicals $R_3$, $R_4$, and $R_5$ represent alkyl, they may be straight or branched $C_1$–$C_{18}$ alkyl, preferably $C_1$–$C_7$ alkyl, and more preferably $C_1$–$C_4$ alkyl groups. Examples of said alkyl groups are methyl, ethyl, n-propyl, isopropyl, n-butyl, sec-butyl, hexyl, octyl, dodecyl or octadecyl. Substituted alkyl groups $R_3$, $R_4$ and $R_5$ are in particular haloalkyl, cyanoalkyl, hydroxyalkyl or lower alkoxyalkyl, each preferably containing 2 to 4 carbon atoms in the alkyl group, for example, 2-chloroethyl, 2-cyanoethyl, 2-hydroxyethyl, 3-hydroxypropyl, $\beta$-methoxyethyl or $\beta$-ethoxypropyl. The alkoxy substituent may have 1–4 carbon atoms. The polyalkyleneoxy substituent for $R_3$–$R_5$ may have 2–4 carbon atoms in each alkylene group, and may possess from about 3 to 50 alkyleneoxy units and terminated by hydroxy or lower alkoxy, preferably hydroxy.

In a preferred embodiment, each alkyl portion radicals $R_3$, $R_4$ and $R_5$ are alkyl groups of 1 to 4 carbon atoms, most preferably methyl or ethyl groups.

In another preferred embodiment $R_3$, $R_4$ and $R_5$ are $C_1$–$C_4$ alkyl, more preferably methyl groups.

The aryl portion of the $R_3$, $R_4$, or $R_5$ aralkyl is preferably phenyl, or naphthyl, most preferably phenyl, and the alkyl portion is preferably $C_1$–$C_4$ alkylene, most preferably methylene.

In an alternate most preferred embodiment, $R_3$ and $R_4$ are methyl groups and $R_5$ is a benzyl group.

The heterocyclic radical formed by the substituents $R_3$ and $R_4$ together with the common nitrogen atom is for example, pyrrolidino, piperidino, picolino, morpholino, thiomorpholino or piperazino.

Substituents for the pyridinium ring formed by $R_3$, $R_4$ and $R_5$ include lower alkyl, preferably methyl, and lower alkoxy, preferably methoxy. Most preferably the pyridinium ring is unsubstituted.

Possible anions $A^{\ominus}$ are both anions of inorganic acids (for example, the chlorine, bromide, fluoride, iodide, sulfate or phosphate ion) and of organic acids, for example, of aryl, lower alkyl or aryl-lower alkyl sulfonic acids such as the benzene sulfonate, p-toluenesulfonate, methanesulfonate or ethanesulfonate ion, and also the anions of aryl, lower alkyl or aryl-lower alkyl carboxylic acids such as acetate and benzoate ions.

The anion $A^{\ominus}$ preferably denotes chloride, bromide, iodide, methane sulfonate or acetate.

The compounds of formula (I) can be conveniently prepared by reacting fluorinated epoxides of formula (II) with ammonium salts of formula (III).

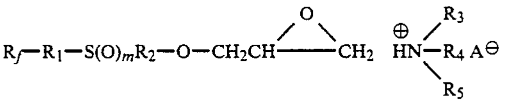

(II) (III)

wherein $R_f$, $R_1$, m, $R_2$, $R_3$, $R_4$, $R_5$ and $A^{\ominus}$ are as previously described, advantageously in the presence or absence of an inert solvent, such as dioxane, diethyl ether, butoxyethoxyethanol or the like, at a temperature of between about 0° C. to 100° C., preferably between 20° C. and about 80° C.

The syntheses of the fluorinated epoxides of formula II are described in U.S. Pat. No. 4,577,036. Typical epoxides which can be used within the context of this invention are:

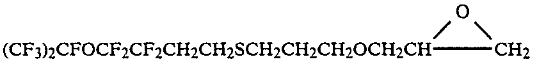

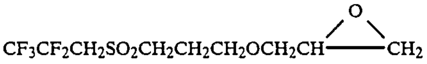

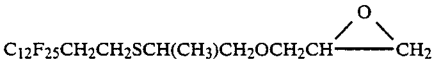

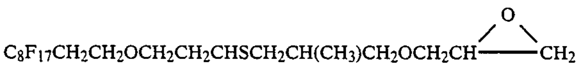

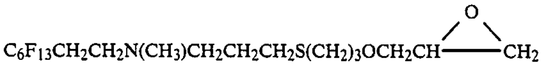

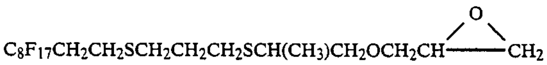

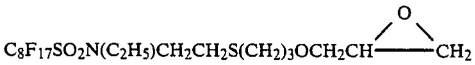

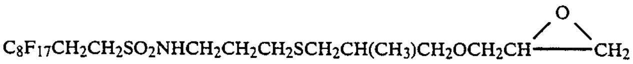

Typical examples of ammonium salts of formula (III) include:

trimethylammonium chloride,
trimethylammonium trifluoroacetate,
benzyldimethylammonium acetate,
pyridinium iodide,
N-methyl morpholine hydrochloride, and
N-ethyl piperidine hydrobromide.

The fluorinated cationic compounds of formula (I) are valuable surfactants. They demonstrate the properties of excellent water solubility and dramatic lowering of the surface tension of aqueous solutions, even at very low concentrations, e.g. <20 dynes/cm at 0.1% active substances, in fresh or sea water.

The invention is illustrated but not limited by the following Examples. Unless otherwise indicated, the percentages are by weight.

EXAMPLE 1

A mixture of trimethylamine hydrochloride (0.84 g, 0.0082 moles) in water (0.84 g, 0.047 moles) is added to a reaction flask. To this is charged a solution of the epoxide

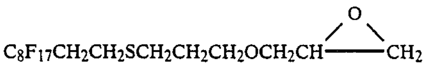

(5.0 g, 0.0084 moles) in 2(2-butoxyethoxy)-ethanol (5.0 g) and the reaction mixture is stirred at 50° for 32 hours. Removal of the solvents affords a yellow gel-like material, which is then slurried in hexane. The hexane is decanted and any remainind hexane is evaporated (draft oven, 100°) to give the pale yellow solid with the structure

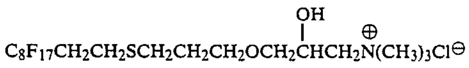

is quantitative yield.

NMR: 1.75 ppm, quintet, 2H, $CH_2\underline{CH_2}$, $CH_2OCH_2$, 2.27 ppm, complex, 2H, $C_8F_{17}\underline{CH_2}CH_2$, 2.59 ppm, complex, 4H, $\underline{CH_2}S\underline{CH_2}$, 3.37 ppm, singlet, 9H, $^{\oplus}N(\underline{CH_3})_3Cl^{\ominus}$ 3.47 ppm, complex 6H, 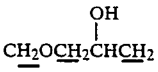

4.35 ppm, complex, 1H, 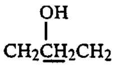

Analysis: Calculated: 33.0% C, 3.6% H, 46.2% F. Found: 33.0% C, 3.8% H, 45.8% F.

EXAMPLES 2-7

Following the procedure outlined in Example 1, the compounds listed in Table 1 were prepared and form part of this invention.

TABLE 1

| Example | $R_f$ | $R_1$ | m | $R_2$ | $R_3$ | $R_4$ | $R_5$ | A |
|---|---|---|---|---|---|---|---|---|
| 2 | $C_6F_{13}$ | $C_2H_4$ | 0 | $C_3H_6$ | $CH_3$ | $CH_3$ | $CH_3$ | Cl |
| 3 | $C_6F_{13}$ | $C_2H_4$ | 0 | $C_3H_6$ | $CH_3$ | $CH_3$ | $CH_3$ | $CH_3\overset{O}{\overset{\Vert}{C}}-O$ |
| 4 | $C_8F_{17}$ | $C_2H_4$ | 0 | $C_3H_6$ | $CH_3$ | $CH_3$ | $CH_3$ | $CH_3\overset{O}{\overset{\Vert}{C}}-O$ |
| 5 | $C_6F_{13}$ | $C_2H_4$ | 0 | $C_3H_6$ | $CH_3$ | $CH_3$ | $C_6H_5CH_2$ | $CH_3\overset{O}{\overset{\Vert}{C}}-O$ |
| 6 | $C_8F_{17}$ | $C_2H_4$ | 0 | $C_3H_6$ | $CH_3$ | $CH_3$ | $C_6H_5CH_2$ | $CH_3\overset{O}{\overset{\Vert}{C}}-O$ |
| 7 | $C_6F_{13}$ | $C_2H_4$ | 2 | $C_3H_6$ | $CH_3$ | $CH_3$ | $CH_3$ | Cl |

EXAMPLE 8

The compounds from the above examples were found to be particularly useful as surfactants in distilled water. The surfactant properties of the aforementioned compounds are summarized in Table 2.

TABLE 2

| Example | Conc. % in Dist. $H_2O$ | Equilibrium Surface Tension $\gamma a$[1] (dynes/cm) | Ross-Miles Foam Ht.[2] mm at 49° Dist. $H_2O$ | Dynamic Surface Tension[3] $\gamma a$ (dynes/cm) 2 sec. | 5 sec. | 10 sec. |
|---|---|---|---|---|---|---|
| 1 | 0.1 | 18.3 | 192 | 36.1 | 31.0 | 28.5 |
| | 0.01 | 20.3 | | | | |
| | 0.001 | 34.5 | | | | |
| 2 | 0.1 | 16.2 | 141 | 31.9 | 25.3 | 20.5 |
| | 0.01 | 18.4 | | | | |
| | 0.001 | 33.1 | | | | |
| 3 | 0.1 | 17.1 | 141 | 39.0 | 34.0 | 29.5 |
| | 0.01 | 18.2 | | | | |
| | 0.001 | 24.8 | | | | |
| 4 | 0.1 | 18.4 | 166 | 41.9 | 38.3 | 36.8 |
| | 0.01 | 19.7 | | | | |
| | 0.001 | 36.4 | | | | |
| 5 | 0.1 | 17.4 | 157 | 21.5 | 17.5 | 16.5 |
| | 0.01 | 19.7 | | | | |
| | 0.001 | 36.4 | | | | |
| 6 | 0.1 | 18.3 | 125 | 42.5 | 38.0 | 35.0 |
| | 0.01 | 19.6 | | | | |
| | 0.001 | 27.1 | | | | |
| 7 | 0.1 | 15.8 | 155 | 32.0 | 22.8 | 18.0 |
| | 0.01 | 19.4 | | | | |
| | 0.001 | 26.7 | | | | |

[1]ASTM method D-1331-56, du Novy tensiometer.
[2]ASTM method D-1173-53, initial foam height in mm.
[3]Drop Weight Technique for the Measurement of Dynamic Surface Tension, C. Jho and R. Burke, Journal of Colloid and Interface Science, Vol. 95, No. 1, September 1983.

EXAMPLE 9

Some of the compounds from the above Examples were found to be particularly useful as surfactants in sea water. The surfactant properties of the aforementioned compounds in sea water are summarized in Table 3.

TABLE 3

| Example | Conc. % in | Equilibrium Surface Tension $\gamma a$[1] (dynes/cm) | Ross-Miles Foam Ht.[2] mm at 49° | Dynamic Surface Tension[3] $\gamma a$ (dynes/cm) 2 sec. | 5 sec. | 10 sec. |
|---|---|---|---|---|---|---|
| 2 | 0.1 | 18.0 | 177 | 21.5 | 19.5 | 19.0 |
| | 0.01 | 17.9 | | | | |

TABLE 3-continued

| Example | Conc. % in | Equilibrium Surface Tension $\gamma a$[1] (dynes/cm) | Ross-Miles Foam Ht.[2] mm at 49° | Dynamic Surface Tension[3] $\gamma a$ (dynes/cm) 2 sec. | 5 sec. | 10 sec. |
|---|---|---|---|---|---|---|
| | 0.001 | 31.6 | | | | |
| 3 | 0.1 | 18.3 | 201 | 24.8 | 20.4 | 18.8 |
| | 0.01 | 18.2 | | | | |
| | 0.001 | 31.3 | | | | |

[1]ASTM method D-1331-56, du Novy Tensiometer.
[2]ASTM method D-1173-53, initial foam height in mm.
[3]Drop Weight Technique for the Measurement of Dynamic Surface Tension, C. Jho and R. Burke, Journal of Colloid and Interface Science, Vol. 95, No. 1, September 1983.

I claim:

1. A compound of the formula $$\left[ R_f-R_1-S(O)_m-R_2-OCH_2\underset{OH}{CH}CH_2\overset{R_3}{\underset{R_4}{N}}-R_5 \right]^{\oplus} A^{\ominus} \qquad (I)$$

wherein $R_f$ is a perfluoroalkyl having up to 18 carbon atoms which is unsubstituted or substituted by a $C_3$–$C_{18}$ perfluoroalkoxy group;

$R_1$ is a $C_1$–$C_7$ alkylene which is uninterrupted or interrupted by a group selected from the group consisting of —O—, —SO—, —$SO_2$—, —$CO_2$—, —NR'—, —$SO_2NR'$— and —CONR'—, wherein R' is hydrogen or $C_1$–$C_7$ alkyl;

m is 0, 1 or 2;

$R_2$ is a $C_2$–$C_4$ alkylene;

$R_3$, $R_4$ and $R_5$ are each independently $C_1$–$C_{18}$ alkyl or $C_7$–$C_{18}$ aralkyl each of which is unsubstituted or substituted by hydroxy, $C_1$–$C_4$ alkoxy, halogen, cyano, or poly ($C_2$–$C_4$) alkyleneoxy having from about 3 to 50 alkyleneoxy units terminated by hydroxy or lower alkoxy; and $A^{\ominus}$ is an anion.

2. The compound of claim 1 wherein $R_f$ has a total of 3–18 carbon atoms.

3. The compound of claim 1 wherein $R_f$ is a straight chained perfluoroalkyl or perfluoroalkoxy-perfluoroalkyl.

4. The compound of claim 1 wherein $R_1$ is an unsubstituted $C_2$–$C_4$ alkylene.

5. The compound of claim 1 wherein $R_1$ is 1,2-ethylene.

6. The compound of claim 1 wherein $R_2$ is a 1,2- or 1,3-$C_3$–$C_4$ alkylene.

7. The compound of claim 1 wherein $R_2$ is propylene or isopropylene.

8. The compound of claim 1 wherein at least one of $R_3$, $R_4$ and $R_5$ is a $C_1$–$C_4$ alkyl.

9. The compound of claim 1 wherein each of $R_3$, $R_4$ and $R_5$ are $C_1$–$C_4$ alkyl.

10. The compound of claim 1 wherein said $R_3$, $R_4$ and $R_5$ alkyl groups are ethyl groups which are unsubstituted or substituted in the $\beta$-position.

11. The compound of claim 1 wherein said alkoxy substituent on said $R_3$, $R_4$ and $R_5$ alkyl is selected from ethoxy and methoxy.

12. The compound of claim 1 wherein said $R_3$, $R_4$ and $R_5$ alkyl is selected from methyl and ethyl and is unsubstituted or substituted as set forth in claim 1.

13. The compound of claim 1 wherein said $R_3$, $R_4$ and $R_5$ are each methyl.

14. The compound of claim 1 wherein $A^{\ominus}$ is selected from $Cl^-$; $F^-$; $Br^-$; sulfate; phosphate; aryl, lower alkyl or aryl-lower alkyl sulfonates; and aryl, lower alkyl or aryl-lower alkyl carboxylates.

15. The compound of claim 14 where said organic sulfonates are selected from benzene sulfonate, p-toluenesulfonate, methanesulfonate, and ethanesulfonate; and said carboxylates are selected from acetate and benzoate.

16. The compound of claim 1 wherein $A^{\ominus}$ is selected from $Cl^-$, $Br^-$, $I^-$, methanesulfonate, and acetate.

* * * * *